(12) United States Patent
Baugh et al.

(10) Patent No.: US 7,351,845 B2
(45) Date of Patent: Apr. 1, 2008

(54) TRANSITION METAL POLYMERIZATION CATALYSTS, THEIR SYNTHESIS AND USE IN OLEFIN POLYMERIZATION

(75) Inventors: Lisa S. Baugh, Ringoes, NJ (US); Enock Berluche, Phillipsburg, NJ (US); Paul V. Hinkle, Wallingford, PA (US); Francis C. Rix, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 129 days.

(21) Appl. No.: 11/333,639

(22) Filed: Jan. 17, 2006

(65) Prior Publication Data

US 2006/0173144 A1 Aug. 3, 2006

Related U.S. Application Data

(60) Provisional application No. 60/648,770, filed on Feb. 1, 2005.

(51) Int. Cl.
*C07F 15/00* (2006.01)
*C07F 9/00* (2006.01)
*C07F 9/02* (2006.01)

(52) U.S. Cl. ............................ 556/21; 556/35; 556/45; 556/136; 556/138; 502/152; 502/162; 526/161; 526/172

(58) Field of Classification Search ................... 556/21, 556/35, 45, 136, 138; 502/152, 162; 526/161, 526/172
See application file for complete search history.

(56) References Cited

FOREIGN PATENT DOCUMENTS

| JP | 2000/128922 | 5/2000 |
|----|-------------|--------|
| WO | 97/37765 | 10/1997 |
| WO | 98/40420 | 9/1998 |
| WO | 00/06299 | 2/2000 |
| WO | 00/59956 | 10/2000 |
| WO | 01/10876 | 2/2001 |
| WO | 01/92342 | 12/2001 |
| WO | 03/031485 | 4/2003 |
| WO | 03/078478 | 9/2003 |

OTHER PUBLICATIONS

Britovsek et al., "Oligomerisation of Ethylene by Bis(imino)pyridyliron and —cobalt Complexes," Chem. Eur. J. 2000, 6, No. 12, 2221-2231.
Walther, D. et al., "Metal Complexes with 2,3-Bis(diphenylphosphino)-1,4-diazadiene Ligands: Synthesis, Structures, and an Intramolecular Metal-Mediated [4+2] Cycloaddition Employing a Benzene Ring as a Dienophile," Inorganic Chemistry 2003, 42, 625-632.
Johnson et al., "New Pd(II)- and Ni(II)-Based Catalysts for Polymerization of Ethylene and α-Olefins," J. Am. Chem. Soc. 1995, 117, 6414-6415 van den Beuken et al., "Oligomerisation of ethene by new palladium iminophosphine catalysts," J. Chem. Soc., Chem. Commun., 1998, 223-224.
Dossett et al., "Steric activation of chelate catalysts: efficient polyketone catalysts based on four-membered palladium(II) diphosphine chelates," J. Chem. Soc. Chem. Commun. 2001, 699-700.
Carter et al., "High activity ethylene trimerisation catalysts based on diphosphine ligands," J. Chem. Soc. Chem. Commun. 2002, 858-859.
Thewissen D.H.M.W. et al., "The Chemistry of Hetero-Allene and—Allylic Derivatives with Rhodium and Iridium II. Rhodium(I)-and Iridium(I)-Phosphine Complexes of Hetero-Allylic Ligands of the Type [$Ph_2PC(X)NR$] (X=S, NR, O) and [$Ph_2P(Q)C(S)NR$] (Q=S, O). Synthesis and $^{31}P$-NMR," Journal of Organometallic Chemistry, vol. 192 (1980), pp. 101-113.
Thewissen D H M W: "The Chemistry of Hetero-Allene and—Allylic Derivatives with Rhodium and Iridium III. Elimination of Hetero-Allene Molecules from Rhodium(I)-Hetero-Allylic-Phosphine Complexes. The First Complex with $\eta^2$-Coordinated $Ph_2PS^-$," Journal of American Organometallic Chemistry, vol. 192 (1980), pp. 115-127.
Done et al., "Novel cationic and neutral Pd(II) complexes bearing imidazole based chelate ligands: synthesis, structural characterisation and catalytic behaviour," Journal of Organometallic Chemistry 607 (2000), 78-92.
Keim et al., "Synthesis, characterization and catalytic activity of Pd(II) and Ni(II) complexes with new cyclic α-diphenylphosphino-ketoimines. Crystal structure of 2,6-diisopropyl-N-(2-diphenylphosphino-cyclopentylidene)aniline and of 2,6-diisopropyl-N-(2-diphenylphosphino-cyclohexylidene)aniline," Journal of Organometallic Chemistry 662 (2002), 150-171.
Schubbe et al., "Struktur der aktiven Spezies und Erklärung des Wanderungs-mechanismus bei der 2,ω-Polymerisation von α-Olefinen," Macromol. Chem. Phys. 1995, 196, 467-478.

(Continued)

*Primary Examiner*—Caixia Lu
(74) *Attorney, Agent, or Firm*—Catherine L. Bell

(57) ABSTRACT

A transition metal ligand complex has the following formula:

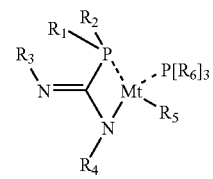

wherein $R_1$ and $R_2$ (each occurrence) independently represent an aryl, alkyl, or cycloalkyl group having up to 20 carbon atoms; $R_3$ and $R_4$ (each occurrence) independently represent an aryl, alkyl, or cycloalkyl group having up to 20 carbon atoms; $R_5$ represents an aryl, alkyl, or cycloalkyl group having up to 20 carbon atoms, provided that $R_4$ and $R_5$ may be joined to form a cyclic structure; $R_6$ represents an alkyl or aryl group having up to 20 carbon atoms; and Mt represents a transition metal selected from Group 7, 8, 9, 10, 11, or 12 of the Periodic Table of the Elements.

19 Claims, No Drawings

OTHER PUBLICATIONS

Vollmerhaus et al., "Synthesis of and Ethylene Polymerization Using Iminophosphonamide Complexes of Group 4," Organometallics 1999, vol. 18, No. 15, 2731-2733.

Chen et al., "Well-Controlled Block Polymerization/Copolymerization of Alkenes and/or Carbon Monoxide by Cationic Palladium Methyl Complexes," Organometallics 2001, 20, 1285-1286.

Reddy et al., "Study of Insertion of Olefins and/or Carbon Monoxide into Phosphine-Imine Palladium Methyl Complexes," Organometallics 2001, 20, 1292-1299.

Cooley et al., "Nickel Ethylene Polymerization Catalysts Based on Phosphourus Ligands," Organometallics 2001, 20, 4769-4771.

Guan et al., "Synthesis of New Phosphine Imine Ligands and Their Effects on the Thermal Stability of Late-Transition-Metal Olefin Polymerization Catalysts," Organometallics 2002, 21, 3580-3586.

Daugulis et al., "Polymerization of Ethylene with Cationic Palladium and Nickel Catalysts Containing Bulky Nonenolizable Imine-Phosphine Ligands," Organometallics 2002, 21, 5926-5934.

Lindenberg et al., "Formation of Novel P- and As-Functionalized Ligands by Insertion Reactions Into the Zr-E Bond of ($\eta^5$-$C_5H_4R)_2ZrCl$ $\{E(SiMe_3)_2\}$ (R=Me, E=P, As; R=H, E=P)," Polyhedron 1996, vol. 15, 1459-1471.

Thewissen et al., "The Reactions of hetero-allenes RN=C=X with phosphine derivatives containing a P-H bond," Rec. Trav. Chim. Pays-Bas 1980, 99, 344-346.

Reetz et al., "2-Pyrimidylphosphines: A New Class of Ligands for Transition Metal Catalysis," Tetrahedron Letters 39 (1998) 7089-7092.

Hey-Hawkins et al., "Insertion von Diphenylcarbodiimid in die Zr-P-Bindung von Cp'$_2$Zr(Cl){P(SiMe$_3$)$_2$} (Cp'=C$_5$H$_4$Me); Molekülstruktur von Cp'$_2$Zr[N(Ph)C{P(SiMe$_3$)$_2$}N(Ph)](Cl)," Z. Naturforsch, B 1993, 48, 951-957.

… (US 7,351,845 B2)

TRANSITION METAL POLYMERIZATION CATALYSTS, THEIR SYNTHESIS AND USE IN OLEFIN POLYMERIZATION

CROSS REFERENCE TO RELATED APPLICATION

This application claims the benefit of priority to U.S. Provisional Patent Application No. 60/648,770, filed Feb. 1, 2005 the disclosure of which is incorporated by reference.

FIELD

This invention relates to transition metal catalysts containing phosphaguanidinate ligands, methods of their synthesis and their use in olefin polymerization, particularly ethylene polymerization.

BACKGROUND

Early transition metal catalysts for producing olefin polymers by coordination polymerization are well-known. Typically these are the traditional Ziegler-type catalysts based on metals from Groups 4 and 5 of the Periodic Table (IUPAC new notation) and the newer metallocene or similar catalysts based on Groups 4 to 8 metals. There is, however, also interest in catalysts based on late transition metals, such as nickel, since these frequently exhibit greater tolerance to polar functional groups than Group 4 to 8 initiators. Polar-tolerant olefin polymerization catalysts may allow the use of cheaper, less pure monomer feeds, and may also offer new product possibilities through the potential incorporation of polar comonomers.

Polymers containing polar functionalities, particularly oxygen- and nitrogen-containing groups, are useful in applications such as flexible packaging, durables, adhesives, and gas- or oil-resistant barrier films. In addition, catalysts which display a high tolerance to polar groups are useful for normal olefin polymerization in the presence of polar poisons such as dimethyl ether.

Considerable research has been directed to the production of ligand frameworks that provide many sites for steric and electronic modification since these offer the possibility of generating a large number of catalysts tailored for specific functions. By way of example, bidentate ligands featuring N,N-, N,O-, P,O-, or N,P-chelation are widely used in the synthesis of transition metal catalysts for olefin oligomerization, trimerization, polymerization, and copolymerization.

Bidentate N,P-binding structures have been incorporated into both highly active Group 4 and 6 based catalysts (Ti, Zr, and Cr) and polar-tolerant late transition metal catalysts (Ni and Pd). For example, Ti, V, Cr, Co, Ni, and Pd complexes containing neutral phosphine-imine or phopshine-amine ligands with four, five, and six membered ring chelation have been used as ethylene oligomerization and polymerization catalysts (see International Patent Publication Nos. WO 03/078478, WO 00/59956, WO 01/92342, and WO 98/40420; Japanese Published Patent Application No. JP2000/128922; Daugulis et al. *Organometallics* 2002, 21, 5926-5934; Guan et al. *Organometallics* 2002; 21, 3580-3586; van den Beuken et al. *J. Chem. Soc., Chem. Commun.* 1998, 223-224; and Keim et al. *J Organomet. Chem.* 2002, 662, 150-171). However, in many cases, the polyethylenes obtained with such catalysts are highly branched and of low molecular weight. Neutral Pd phosphine-imines have also been used for olefin/carbon monoxide (CO) copolymerization (see, for example, Chen et al. *Organometallics* 2001, 20, 1285-1286; and Reddy et al. *Organometallics* 2001, 20, 1292-1299).

In addition to these species incorporating neutral bidentate ligands, Ni complexes incorporating monoanionic phosphine-amide ligands with four- and five-membered ring chelation have been shown to be active for ethylene polymerization and ethylene/norbornene copolymerization (see International Patent Publication Nos. WO 03/31485 and WO 01/92342).

Mixed nitrogen-phosphorus ligands having a total of three N or P atoms, yet exhibiting a bidentate binding mode, have also been used in both early and late transition metal catalysts. For example, neutral P,N,P ligands have been incorporated into complexes of Cr (for ethylene trimerization), Ni (for olefin polymerization), and Pd (for olefin/CO copolymerization) (see, for example, International Patent Publication Nos. WO 01/10876, WO 00/06299, and WO 97/37765; Cooley et al. *Organometallics* 2001, 20, 4769-4771; Carter et al. *J. Chem. Soc., Chem. Commun.* 2002, 858-859; and Dossett et al. *J. Chem. Soc., Chem. Commun.* 2001, 699-700). These complexes have four-membered ring ligand chelation with the two P atoms binding to the metal center. The two P atoms are linked via direct P—N bonds to a single non-binding nitrogen atom.

Similarly, monoanionic iminophosphonamide N,P,N ligands having direct N—P—N linkages and undergoing four-membered ring N,N-ligand coordination have been used to prepare Ti, Zr, and Ni complexes active for olefin polymerization. See, for example, Vollermaus et al. *Organometallics* 1999, 18, 2731-2733 and Schubbe et al. *Macromol. Chem. Phys.* 1995, 196, 467-478.

Phosphine-imidazoles and pyrimidyl-phosphines are N,N,P ligands containing two nitrogen atoms and one phosphorus atom, all of which are attached to a central carbon atom, wherein the two N atoms form part of an unsaturated five- or six-membered heterocylic ring. Pyrimidyl-phosphines are neutral, whereas phosphine-imidazoles may be may be neutral or monoanionic depending on the pattern of N-substitution. Due to the heterocyclic ring structure, neither phosphine-imidazoles or pyrimidyl-phosphines can be subjected to independent variation of the substituents present at each N atom, nor can they undergo bidentate N,N-binding. These ligands tend to bind to a metal in a monodentate fashion through only one donor atom, or to two metals simultaneously in a bridging (dimeric) fashion, which may negatively affect catalytic activity. For example, dimeric Pd complexes with bridging phosphine-imidazole ligands have been found to be inactive for ethylene/CO polymerization by Done et al. (*J. Organomet. Chem.* 2000, 607, 78-92). However, in contrast, a monomeric pyrimidyl-phosphine Pd complex with bidentate, four-membered ring P,N coordination was found to be active for alkyne carbonylation by Reetz et al. (*Tetrahedron Lett.* 1998, 39, 7089-7092).

International Patent Publication No. WO 01/92342 describes monoanionic, bidentate N,N,P ligands and Ni complexes of such ligands that are active for olefin polymerization. In these complexes, the Ni atom is bound to the P atom and to one negatively charged N atom in a five-membered ring arrangement. However, although the two N atoms are bound to a single central carbon, the P atom is not bound to the same central carbon atom.

Phosphaguanidinate ligands are monoanionic N,N,P ligands in which the phosphorus atom and two nitrogen atoms are all attached to a central carbon atom and are not part of a heterocyclic structure. A phosphaguanidinate ligand can undergo binding to a transition metal through one N atom and the P atom or, alternately through both N atoms, in a bidentate, four-membered-ring fashion.

Phosphaguanidinate ligands of the structure [Ph$_2$PC(N-p-tolyl)(NH-p-tolyl)] and complexes of the structure [Ph$_2$PC(N-p-tolyl)(N-p-tolyl)]Mt(PPh$_3$)$_2$ (where Mt is Rh or Ir), which have four-membered-ring P,N-coordination, have been prepared by Thewissen et al. (*J. Organomet. Chem.* 1980, 192, 101-113 and 115-127 and *Rec. Trav. Chim. Pays-Bas* 1980, 99, 244-246). These ligands and complexes have not been used for polymerization reactions, lack ortho-substitution on their N-aryl(tolyl) substituents, and are unstable under certain conditions and to certain reactants. N-aryl ortho-substituents are known to play an important role in manipulating the behavior of mid- and late-transition metal olefin polymerization/oligomerization catalysts (see, for example, Johnson et al. *J. Am. Chem. Soc.* 1995, 117, 6414-6415 and Britovsek et al. *Chem. Eur. J.* 2000, 6, 2221-2231).

Phosphaguanidinate complexes of Zr containing four-membered ring N,N binding have been prepared via insertion of an RN═C═NR fragment (where R is phenyl or isopropyl) into the Zr—P bond of (Cp)$_2$ZrCl {P(SiMe$_3$)$_2$} (where Cp=C$_5$H$_5$ or C$_5$H$_4$Me). See Hey-Hawkins et al. *Z. Naturforsch, B* 1993, 48, 951-957 and Lindenberg et al. *Polyhedron* 1996, 15, 1459-1471. These phosphaguanidinate ligands have silyl rather than carbon substituents at the P atom and the ligand salt Li[P(SiMe$_3$)$_2$C(NPh)(NPh)] could not be successfully prepared by reaction of Li[P(SiMe$_3$)$_2$] with PhN═C═NPh in the absence of Zr. These ligands and complexes have also not been used for polymerization reactions.

SUMMARY

In one aspect, the present invention is directed to a transition metal ligand complex having the following formula:

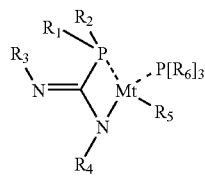

wherein R$_1$ and R$_2$ (each occurrence) independently represent an aryl, alkyl, or cycloalkyl group having up to 20 carbon atoms, preferably a t-butyl group; R$_3$ and R$_4$ (each occurrence) independently represent an aryl, alkyl, or cycloalkyl group having up to 20 carbon atoms, preferably an aryl group; R$_5$ represents an aryl, alkyl, or cycloalkyl group having up to 20 carbon atoms, preferably phenyl, provided that R$_4$ and R$_5$ may be joined to form a cyclic structure in which case R$_5$ is preferably alkyl; R$_6$ represents an alkyl or aryl group having up to 20 carbon atoms, preferably phenyl; and Mt represents a transition metal selected from Group 7, 8, 9, 10, 11, or 12 of the Periodic Table of the Elements.

In one embodiment, one or each of R$_3$ and R$_4$ represents an aryl group bearing an alkyl substituent having up to 8 carbons at one or both of the ortho (2,6-) positions to the aryl-N bond. In this embodiment, it is preferable that both ortho positions bear substituents, and that the substituents be, independently, methyl or isopropyl, most preferably isopropyl. In one preferred embodiment, R$_4$ represents an aryl group bearing an alkyl substituent having up to 8 carbons at one or both of the ortho (2,6-) positions to the aryl-N bond, and R$_4$ and R$_5$ are joined through an alkyl substituent of R$_4$ such that the transition metal ligand complex of the invention has the following formula:

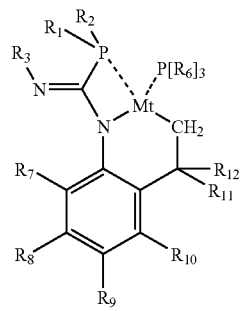

wherein R$_1$, R$_2$, R$_3$, R$_6$, and Mt are as defined above, and R$_7$, R$_8$, R$_9$, R$_{10}$, R$_{11}$, and R$_{12}$ (each occurrence) independently represent hydrogen or an alkyl group having up to 8 carbon atoms. It is most preferred that R$_7$ is isopropyl, R$_8$, R$_9$, R$_{10}$, and R$_{12}$ are hydrogen, and R$_{11}$ is methyl.

Conveniently, the transition metal, Mt, is selected from Groups 7 to 12, preferably Groups 10 to 12, of the Periodic Table of Elements and typically is nickel or palladium. Generally, the transition metal is divalent.

In a further aspect, the invention resides in an olefin polymerization catalyst system comprising a transition metal ligand complex according to said one aspect of the invention and, optionally, an activator.

In yet a further aspect, the invention resides in a process for polymerizing ethylene in the presence of a catalyst system according to said further aspect of the invention.

DETAILED DESCRIPTION

For the purposes of this invention and the claims thereto when a polymer is referred to as comprising an olefin, the olefin present in the polymer is the polymerized form of the olefin. In addition, a reactor is any container(s) in which a chemical reaction occurs.

As used herein, the new numbering scheme for the Periodic Table of Elements is used as set out in CHEMICAL AND ENGINEERING NEWS 1985, 63(5), 27.

As used herein, the phrase "having the formula" is not intended to be limiting and is used in the same way that "comprising" is used. Likewise, it is understood that the formulae depicted herein are representations of the compounds and may not indicate the spatial relationships between the groups. For example the formulae depicted herein do not indicate specific cis or trans relationships between the groups. The terms "independently represent" and "independently selected from" are used herein to indicate that the designated groups, e.g., R$_1$ and R$_3$, can be identical or different. As used herein, the term "catalyst system" is intended to refer to a composition that is capable of and used to initiate polymerization. Thus, the term "catalyst system" may include the transition metal ligand complex of the invention alone or the combination of transition metal ligand complex and an activator. In this respect, the term "activator" is used to mean a compound that increases the rate at which the transition metal ligand complex polymerizes olefin monomers and/or a compound that affects the molecular weight, degree of branching, comonomer content, or other properties of the resultant polymer. The term "catalyst system" also includes intermediates formed during polymerization, whether transient or not, such as metal hydrides formed by chain transfer. The catalyst system of the invention may also include other components, such as a support.

The term "aryl" is used herein to refer to an aromatic substituent which may be a single aromatic ring or multiple aromatic rings which are fused together or linked covalently. The aromatic ring(s) may include phenyl, naphthyl, anthracenyl, and biphenyl. The term "aryl" is also used herein to include "substituted aryl" in which one or more hydrogen atoms attached to any carbon atom on an aromatic ring is replaced by one or more groups, such as alkyl or cycloalkyl.

Transition Metal Ligand Complex

The present invention provides a novel transition metal ligand complex having the following formula:

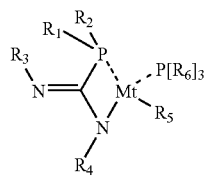

wherein $R_1$ and $R_2$ (each occurrence) independently represent an aryl, alkyl, or cycloalkyl group having up to 20 carbon atoms; $R_3$ and $R_4$ (each occurrence) independently represent an aryl, alkyl, or cycloalkyl group having up to 20 carbon atoms; $R_5$ represents an aryl, alkyl, or cycloalkyl group having up to 20 carbon atoms, provided that $R_4$ and $R_5$ may be joined to form a cyclic structure; $R_6$ represents an alkyl or aryl group having up to 20 carbon atoms; and Mt represents a transition metal selected from Group 7, 8, 9, 10, 11, or 12 of the Periodic Table of the Elements.

Conveniently, one or each of $R_1$ and $R_2$ represents a t-butyl group.

Conveniently, $R_3$ represents an aryl group, particularly an aryl group bearing an alkyl substituent having up to 8 carbons at one or both of the ortho (2,6-) positions to the aryl-N bond. In this embodiment, it is preferable that both ortho positions bear alkyl substituents, and that the substituents be, independently, methyl or isopropyl, most preferably isopropyl.

Conveniently, $R_4$ also represents an aryl group, particularly an aryl group bearing an alkyl substituent having up to 8 carbons at one or both of the ortho (2,6-) positions to the aryl-N bond. In one embodiment, both ortho positions bear alkyl substituents, typically with the substituents being, independently, methyl or isopropyl, most preferably isopropyl. In another embodiment, $R_4$ and $R_5$ are joined through the alkyl substituent of $R_4$ such that the transition metal ligand complex of the invention has the following formula:

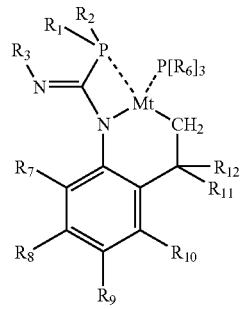

wherein $R_1$, $R_2$, $R_3$, $R_6$, and Mt are as defined above and $R_7$, $R_8$, $R_9$, $R_{10}$, $R_{11}$, and $R_{12}$ (each occurrence) independently represent hydrogen or an alkyl group having up to 8 carbon atoms. Preferably, $R_7$ is isopropyl, $R_8$, $R_9$, $R_{10}$, and $R_{12}$ are hydrogen, and $R_{11}$ is methyl.

Conveniently, $R_5$ represents a phenyl group or, alternately, is joined with $R_4$ to form a cyclic structure.

Conveniently, $R_6$ represents a phenyl group.

The transition metal Mt of the complex can be any transition metal selected from Groups 7 to 12 of the Periodic Table of Elements, and preferably is a late transition metal from selected Groups 10 to 12, such as nickel or palladium. Generally, the transition metal is divalent.

The ligands of the invention comprise two nitrogen atoms and one phosphorus atom, in which all three of the hetero (N,N, P) atoms are bound to a single, central carbon atom. The ligands of the present invention preferably have N-aryl substituents with di-ortho-alkyl substitution. These ligands offer multiple binding possibilities in that they can potentially bind to a metal in a monoanionic, bidentate fashion using one N and one P atom, or alternately with both N atoms, in a four-membered ring arrangement. In the transition metal complexes of these ligands, for example, the Ni complexes, the Ni atom may be bound to the neutral P atom and to the negatively charged N atom in a four-membered ring arrangement.

A representative example of the transition metal ligand complex of the invention includes:

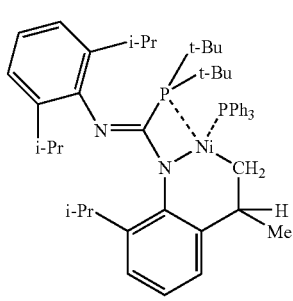

IIa

For purposes of this invention and the claims thereto, Et is ethyl, i-Pr is isopropyl, t-Bu is tertiary butyl, Ph is phenyl, and Me is methyl.

In another embodiment of the invention, the group $P[R_6]_3$ may be replaced by another neutral donor ligand, such as a nitrile, particularly acetonitrile.

Method of Making the Transition Metal Ligand Complex

The transition metal ligand complexes of the invention are readily prepared by contacting a lithium di-alkyl(or di-aryl) phosphide with a 1,3-disubstituted carbodiimide in an ethereal solvent, to form the lithium salt of the desired ligand. Representative examples of such salts include:

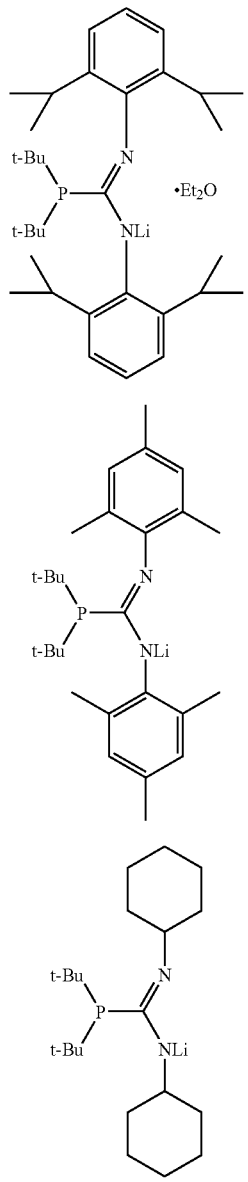

The lithium salt is then contacted with a divalent transition metal alkyl compound, such as bis(triphenylphosphine)nickel(II)phenyl bromide, as described in the Examples.

Olefin Polymerization Catalyst System

The transition metal ligand complexes according to the invention are particularly useful in catalyst systems for polymerizing olefins. In such a catalyst system the transition metal ligand complex is optionally combined with an activator which increases the rate at which the complex polymerizes olefin monomers. An activator may also affect the molecular weight, degree of branching, comonomer content, and other properties of the resultant polymer.

Suitable activators for use in the catalyst system of the invention include neutral Lewis acid phosphine sponges that are capable of binding to the neutral ligand group $P[R_6]_3$ more strongly than the transition metal atom of the transition metal ligand complex. These activators are believed to abstract the $P[R_6]_3$ group from the metal center, yielding a vacant coordination site for olefin coordination and a byproduct molecule of $P[R_6]_3$-phosphine adduct. For example, tris(pentafluorophenyl)borane is believed to abstract a phosphine ligand from a transition metal ligand complex having the formula (phosphaguanidinate)MtR$_5$[P(R$_6$)$_3$] to yield an olefin-binding (phosphaguanidinate)MtR$_5$ complex and a $[P(R_6)_3][B(C_6F_5)_3]$ complex. See Wang et al., *Organometallics* 1998, 17, 3149-3151 for further explanation of how phosphine sponges perform. One may also use other neutral boranes as activators, particularly perfluoroarylboranes.

In general, where the catalyst system of the invention includes an activator, the transition metal ligand complex and the activator are combined in ratios of about 1:20 to 1:1.

Catalyst Supports

The catalyst system of this invention may include a support material or carrier. For example, the transition metal ligand complex and optionally one or more activators may be deposited on, contacted with, vaporized with, bonded to, incorporated within, or adsorbed, or absorbed in or on, one or more supports or carriers.

The support material can be any of the conventional support materials, but preferably is a porous support material, for example, talc, inorganic oxides, or a zeolite. Other support materials include resinous support materials, such as polystyrene; functionalized or crosslinked organic supports, such as polystyrene-divinyl benzene polyolefins or other polymeric compounds; inorganic chlorides; clays; any other organic or inorganic support material; and mixtures thereof.

Preferred support materials are inorganic oxides that include Group 2, 3, 4, 5, 13, or 14 metal oxides. These include silica, which may or may not be dehydrated, fumed silica, alumina (see International Patent Publication No. WO 99/60033), silica-alumina, and mixtures thereof. Other useful supports include magnesia, titania, zirconia, magnesium chloride (see U.S. Pat. No. 5,965,477), montmorillonite (see European Patent No. 0 511 665 B1), phyllosilicate, zeolites, talc, clays (see U.S. Pat. No. 6,034,187), and the like. Also, combinations of these support materials may be used, for example, silica-chromium, silica-alumina, and silica-titania. Additional support materials may include those porous acrylic polymers described in European Patent No. 0 767 184 B1. Other support materials include nanocomposites as described in International Patent Publication No. WO 99/47598, aerogels as described in International Patent Publication No. WO 99/48605, spherulites as described in U.S. Pat. No. 5,972,510, and polymeric beads as described in International Patent Publication No. WO 99/50311.

It is preferred that the support material, most preferably an inorganic oxide, has a surface area in the range of from about 10 to about 700 m²/g, a pore volume in the range of from about 0.1 to about 4.0 cc/g, and an average particle size in the range of from about 5 to about 500 μm. More preferably, the surface area of the support material is in the range of from about 50 to about 500 m²/g, the pore volume is in the range of from about 0.5 to about 3.5 cc/g, and the average particle size is in the range of from about 10 to about 200 μm. Most preferably, the surface area of the support material is in the range of from about 100 to about 400 m²/g, the pore volume is in the range from about 0.8 to about 3.0 cc/g, and the average particle size is in the range from about 5 to about 100 µm. The average pore size of the support material useful in the invention is typically in the range of from 10 to 1000 Å, preferably in the range of from about 50 to about 500 Å, and most preferably in the range of from about 75 to about 350 Å.

Monomers

The catalyst system described herein may be used for the polymerization of one or more olefin monomers. Typical monomers include monomers having from 2 to 30 carbon atoms, preferably 2 to 12 carbon atoms, and more preferably 2 to 8 carbon atoms. Useful monomers include linear, branched, or cyclic olefins, especially linear, branched, or cyclic alpha-olefins; linear, branched, or cyclic dienes, especially linear or branched alpha-omega dienes and aromatic divinyl dienes; and linear, branched, or cyclic polyenes. Useful monomers may also include aromatic group-containing olefins.

Preferred linear alpha-olefins include C2 to C16 alpha-olefins, more preferably ethylene, propylene, 1-butene, 1-pentene, 1-hexene, 1-octene, 1-decene, and 1-hexadecene, even more preferably ethylene, propylene, and 1-butene. Preferred branched alpha-olefins include 4-methyl-1-pentene, 3-methyl-1-pentene, 3,5,5-trimethyl-1-hexene, and 5-ethyl-1-nonene.

Suitable cyclic olefin monomers can contain up to 30 carbon atoms and have at least one polymerizable olefinic group that is either pendant to a non-aromatic cyclic structure or is part of the cyclic structure. The cyclic structure may also be further substituted by one or more hydrocarbyl groups such as, but not limited to, C1 to C10 alkyl groups. Preferred cyclic olefin monomers include vinylcyclohexane, vinylcyclopentane, cyclopentene, cyclohexene, cyclobutene, and vinyladamantane.

Preferred aromatic-group-containing olefin monomers can also contain up to 30 carbon atoms. Suitable aromatic-group-containing monomers comprise at least one aromatic structure and at least one polymerizable double bond such that after polymerization, the aromatic structure will be pendant from the polymer backbone. The aromatic-group containing monomer may further be substituted with one or more hydrocarbyl groups, including but not limited to C1 to C10 alkyl groups. Preferred aromatic monomers include styrene, alpha-methylstyrene, para-alkylstyrenes, vinyltoluenes, vinylnaphthalene, 4-phenyl-1-butene, allyl benzene, and indene, especially styrene, para-methylstyrene, 4-phenyl-1-butene, and allyl benzene.

Diene monomers useful in this invention include any hydrocarbon structure, preferably C4 to C30, having at least two olefins, wherein both of the olefins may be potentially incorporated into a polymer or, alternatively, wherein the second olefin is not incorporated but may be separately reacted in a post-polymerization step such as crosslinking or functionalization. It is further preferred that the diene monomers be selected from alpha, omega-diene monomers (di-vinyl monomers). More preferably, the diene monomers are linear di-vinyl monomers, most preferably those containing from 4 to 30 carbon atoms.

Examples of di-vinyl diene monomers include the alpha, omega-forms of butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene and triacontadiene. Particularly preferred di-vinyl dienes include 1,6-heptadiene, 1,7-octadiene, 1,8-nonadiene, 1,9-decadiene, 1,10-undecadiene, 1,11-dodecadiene, 1,12-tridecadiene, and 1,13-tetradecadiene.

The di-vinyl diene monomer may also comprise an aromatic di-vinyl diene, such as 1,4-divinylbenzene.

Alternately, the diene monomer may be selected from a linear, branched, or cyclic diene having a non-di-vinyl structure. These diolefins may have a structure in which one olefin is a vinyl group and the remaining olefin is an internal 1,2-disubstituted, trisubstituted, or tetrasubstituted olefin. Preferred non-di-vinyl diolefins include 7-methyl-1,6-octadiene, 1,4-hexadiene, 4-vinyl-1-cyclohexene, vinylnorbornene, and ethylidene norbornene. The non-di-vinyl structure may alternately comprise a diolefin in which both olefins are part of a cyclic aliphatic ring, rather than the first olefin comprising a vinyl group. Preferred diolefins having this structure are cyclopentadiene, cyclohexadiene, norbornadiene, dicyclopentadiene, and higher ring containing diolefins with or without substituents at various ring positions.

Conveniently, one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

In one preferred embodiment the process of the invention relates to the polymerization of ethylene and at least one alpha-olefin comonomer having from 3 to 8 carbon atoms, preferably 4 to 8 carbon atoms. Particularly, the comonomers are propylene, 1-butene, 4-methyl-1-pentene, 3-methyl-1-pentene, 1-hexene, and 1-octene, the most preferred being 1-hexene, 1-butene, and 1-octene.

In another preferred embodiment the polymer produced herein is a propylene homopolymer or copolymer. The comonomer is preferably ethylene or a C4 to C20 linear, branched, or cyclic monomer, and in one embodiment is a C4 to C12 linear or branched monomer, preferably 1-butene, 1-pentene, 1-hexene, 1-heptene, 1-octene, 1-nonene, 1-decene, 1-dodecene, 4-methyl-1-pentene, 3-methyl-1-pentene, 3,5,5-trimethyl-1-hexene, and 5-ethyl-1-nonene.

In another embodiment ethylene or propylene is polymerized with at least two different comonomers to form a terpolymer or multipolymer. The preferred comonomers are an alpha-olefin monomer or a combination of alpha-olefin monomers, more preferably those alpha-olefin monomer(s) having 4 to 8 carbon atoms, optionally with at least one diene monomer also included in the comonomer mixture. The preferred terpolymers include the combinations ethylene/1-butene/1-hexene, ethylene/propylene/1-butene, propylene/ethylene/1-hexene, and ethylene/propylene/norbornene.

In another embodiment, the olefin polymer comprises:
  at least one first monomer present at from 40 to 95 mole %, preferably 50 to 90 mole %, more preferably 60 to 80 mole %, and
  at least one second monomer present at from 5 to 60 mole %, preferably 10 to 50 mole %, more preferably 20 to 40 mole %, and
  at least one third monomer present at from 0 to 10 mole %, preferably from 0.5 to 5 mole %, more preferably 1 to 3 mole %.

Typically, the first monomer comprises one, or a mixture of, C3 to C10 linear, branched, or cyclic alpha-olefins, including propylene, butene (and all alpha-olefinic isomers thereof), pentene (and all alpha-olefinic isomers thereof), hexene (and all alpha-olefinic isomers thereof), heptene (and all alpha-olefinic isomers thereof), and octene (and all alpha-olefinic isomers thereof). Preferred monomers include propylene, 1-butene, 1-hexene, 1-octene, and 1-decene.

The second monomer may comprise one, or a mixture of, C2 to C40 linear, branched, cyclic, or aromatic group-containing alpha-olefins, including ethylene, propylene, 1-butene, 1-pentene, 1-hexene, 1-heptene, 1-octene, 1-nonene, 1-decene, 1-undecene, 1-dodecene, 1-hexadecene, styrene, 3,5,5-trimethyl-1-hexene, 3-methyl-1-pentene, 4-methyl-1-pentene, 5-ethyl-1-nonene, norbornene, and cyclopentene.

The third monomer may comprise one, or a mixture of, C2 to C40 linear, branched, cyclic, or aromatic group-containing alpha-olefins or dienes, including ethylene, propylene, 1-butene, 1-pentene, 1-hexene, 1-heptene, 1-octene, 1-nonene, 1-decene, 1-undecene, 1-dodecene, 1-hexadecene, butadiene, 1,5-hexadiene, 1,6-heptadiene, 1,4-pentadiene, 1,7-octadiene, 1,8-nonadiene, 1,9-decadiene, 1,11-dodecadiene, styrene, 3,5,5-trimethyl-1-hexene, 3-methyl-1-pentene, 4-methyl-1-pentene, 5-ethyl-1-nonene, and cyclopentadiene.

Polymerization Process

The catalyst system described above is suitable for use in a solution, bulk, gas phase, supercritical, or slurry polymerization process or a combination of such processes.

In one embodiment, this invention is directed toward solution, bulk, slurry, gas phase, or supercritical polymerization processes involving the polymerization of one or more of monomers having from 2 to 30 carbon atoms, preferably 2 to 12 carbon atoms, and more preferably 2 to 10 carbon atoms. Preferred monomers include one or more alpha-olefin monomers, particularly ethylene, propylene, 1-butene, 1-pentene, 4-methyl-1-pentene, 1-hexene, 1-octene, 1-decene, and 3-methyl-1-pentene; cyclic olefin monomers, particularly norbornenes; and combinations of such monomers. Preferably a homopolymer or copolymer of propylene is produced. In another embodiment, both a homopolymer of propylene and a copolymer of propylene and one or more of the monomers listed above are produced.

One or more reactors in series or in parallel may be used in the present invention. Additionally, if desired, more than one catalyst system can be used. The components of each catalyst system (transition metal ligand complex and, optionally, activator) may be delivered as solids, powders, solutions, or slurries, and may be delivered separately to the reactor, reacted in-line just prior to the reactor, or pre-reacted and subsequently pumped to the reactor as a single solution or slurry. A preferred operation for dual catalyst systems is to deliver each catalyst system as a solution, reacting each transition metal ligand complex with activator (if used) in-line just prior to the reactor. For more information on methods to introduce multiple catalyst systems into reactors, see U.S. Pat. No. 6,399,722 and International Patent Publication No. WO 01/30862. While these references emphasize gas phase reactors, the techniques described are equally applicable to other types of reactors, including continuous stirred tank reactors and slurry loop reactors. Polymerizations are carried out either in single reactor operation, in which monomer, comonomer(s), and catalyst system component(s) are added continuously to a single reactor, or in series reactor operation, in which the above components are added to each of two or more reactors connected in series. The components of all catalyst system(s) present can be added to the first reactor in the series. The components of each catalyst system, when multiple catalyst systems are used, may also be added to separate reactors, with one catalyst system being added to the first reactor, and additional catalyst system(s) being added to the subsequent reactor(s).

In one embodiment 500 ppm or less of hydrogen is added to the polymerization, or 400 ppm or less, or 300 ppm or less. In other embodiments at least 50 ppm of hydrogen is added to the polymerization, or 100 ppm or more, or 150 ppm or more.

Gas Phase Polymerization

Generally, in a fluidized gas bed process used for producing polymers according to this invention, a gaseous stream containing one or more monomers is continuously cycled through a fluidized bed in the presence of a catalyst system under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661, and 5,668,228).

Slurry Phase Polymerization

A slurry polymerization process generally operates at pressures of about 1 atmosphere to about 50 atmospheres or higher (15 psig to 735 psig; 103 kPa to 5068 kPa), and temperatures of about 0° C. to about 120° C. In a slurry polymerization, a suspension of solid particulate polymer is formed in a liquid polymerization diluent medium to which monomer, comonomers, and catalyst system components are added. The suspension, including diluent, is intermittently or continuously removed from the reactor and the volatile components are separated from the polymer and recycled, optionally after a distillation, back to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process is typically operated above the reaction diluent critical temperature and pressure (e.g. supercritical conditions). Preferably, a hexane or an isobutane medium is employed.

A preferred polymerization technique useful in the invention is a slurry process in which the reactor temperature is kept below the temperature at which the polymer goes into solution. Such technique is well known in the art, and described in, for instance, U.S. Pat. No. 3,248,179. The preferred temperature in such a process is from about 85° C. to about 110° C. Two preferred polymerization methods for the slurry process are those employing a loop reactor and those utilizing a plurality of stirred reactors in series or parallel or combinations thereof. Non-limiting examples of slurry processes include continuous loop and stirred tank processes. Other examples of slurry processes are described in U.S. Pat. No. 4,613,484.

In one embodiment of this preferred technique, the slurry process is carried out continuously in a loop reactor. The catalyst system components, taken together as a slurry in isobutane or as a dry free flowing powder, are injected regularly into the reactor loop, which is itself filled with a circulating slurry of growing polymer particles in a diluent of isobutane that contains monomer and comonomer.

Hydrogen, optionally, may be added as a molecular weight control agent. The reactor is maintained at a pressure of about 3620 kPa (36.2 bar) to about 4309 kPa (43.1 bar), and a temperature of about 60° C. to about 104° C., depending on the desired polymer melting characteristics. Reaction heat is removed through the loop wall since much of the loop reactor is in the form of a double-jacketed pipe. The slurry is allowed to exit the reactor (at regular intervals or continuously) to a heated low-pressure flash vessel, rotary dryer, and nitrogen purge column in sequence for removal of the isobutane diluent and all unreacted monomer and comonomer(s).

Typically, the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Homgeneous, Bulk, or Solution Phase Polymerization

The catalyst system described herein can be used advantageously in homogeneous solution polymerization processes. Generally this involves polymerization in a continuous reactor or batch reactor in which the polymer formed, and the monomer(s) and catalyst system components added, are agitated to reduce or avoid concentration gradients. Suitable processes may operate above the melting point of the polymers at high pressures, from 0.1 to 3000 bar (1 to 30,000 MPa), preferably from 0.1 bar to 1600 bar (1 to 16,000 MPa), most preferably from 1.0 to 500 bar (10 to 5000 MPa). Suitable processes may also operate below the melting point of the polymer to be produced.

Temperature control in the reactor is obtained by balancing the heat of polymerization with reactor cooling. Cooling may be achieved by reactor jackets, cooling coils, auto refrigeration, pre-chilled feeds, vaporization of a liquid medium (diluent, monomer(s), or solvent), or any combination of these techniques. Adiabatic reactors with pre-chilled feeds may also be used. The reactor temperature desired depends on the catalyst system used.

In one embodiment 500 ppm or less of hydrogen is added to the polymerization, or 400 ppm or less, or 300 ppm or less. In other embodiments at least 50 ppm of hydrogen is added to the polymerization, or 100 ppm or more, or 150 ppm or more.

Each of these processes may be employed in single reactor or parallel or series reactor configurations. The liquid processes comprise contacting olefin monomer(s) with the above described catalyst system in a suitable diluent or solvent and allowing said monomer(s) to react for a sufficient time to produce the desired polymer(s). Hydrocarbon solvents are suitable, both aliphatic and aromatic. Alkanes, such as hexane, pentane, isopentane, and octane, are preferred.

The process can be carried out in a continuous stirred tank reactor, batch reactor, or plug flow reactor, or in multiple reactors operated in series or parallel. These reactors may or may not have internal cooling or heating and the monomer feed may or may not be refrigerated. See the general disclosure of U.S. Pat. No. 5,001,205 for general process conditions. See also, International Patent Publication Nos. WO 96/33227 and WO 97/22639.

In another embodiment, this invention relates to:
1. A transition metal ligand complex having the following formula:

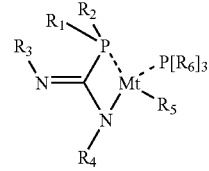

wherein $R_1$ and $R_2$ (each occurrence) independently represent an aryl, alkyl, or cycloalkyl group having up to 20 carbon atoms; $R_3$ and $R_4$ (each occurrence) independently represent an aryl, alkyl, or cycloalkyl group having up to 20 carbon atoms; $R_5$ represents an aryl, alkyl, or cycloalkyl group having up to 20 carbon atoms, provided that $R_4$ and $R_5$ may be joined to form a cyclic structure; $R_6$ represents an alkyl or aryl group having up to 20 carbon atoms; and Mt represents a transition metal selected from Group 7, 8, 9, 10, 11, or 12 of the Periodic Table of the Elements.
2. The complex of item 1 wherein one or each of $R_1$ and $R_2$ represents a t-butyl group.
3. The complex of item 1 or 2 wherein one or each of $R_3$ and $R_4$ represents an aryl group.
4. The complex of any of items 1, 2, or 3 wherein one or each of $R_3$ and $R_4$ represents an aryl group bearing an alkyl substituent having up to 8 carbons at one or both of the ortho (2,6-) positions to the respective aryl-N bond.
5. The complex of item 4 and bearing said alkyl substituents at both of the ortho (2,6-) positions to the respective aryl-N bond.
6. The complex of item 5 wherein each alkyl substituent is independently selected from methyl and isopropyl.
7. The complex of item 5 wherein each alkyl substituent is isopropyl.
8. The complex of any of items 1 to 7 wherein $R_5$ represents a phenyl group.
9. The complex of any of items 1 to 8 wherein $R_6$ represents a phenyl group.
10. The complex of any of items 1, 2, 3, 4, 5, 6, or 7 wherein $R_4$ and $R_5$ are joined to form a cyclic structure.
11. The complex of item 10 wherein $R_6$ represents a phenyl group.
12. The complex of any of items 1, 2, 3, 4, 5, or 6 wherein $R_4$ represents an aryl group bearing an alkyl substituent having up to 8 carbons at one or both of the ortho (2,6-) positions to the aryl-N bond, and $R_4$ and $R_5$ are joined such that the complex has the following formula:

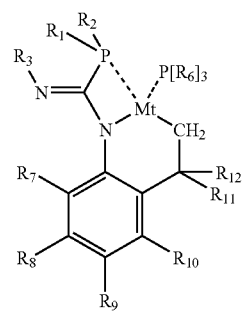

wherein $R_1$ and $R_2$ (each occurrence) independently represent an aryl, alkyl, or cycloalkyl group having up to 20 carbon atoms; $R_3$ represent an aryl, alkyl, or cycloalkyl group having up to 20 carbon atoms; $R_6$ represents an alkyl or aryl group having up to 20 carbon atoms; Mt represents a transition metal selected from Group 7, 8, 9, 10, 11, or 12 of the Periodic Table of the Elements; and $R_7$, $R_8$, $R_9$, $R_{10}$, $R_{11}$, and $R_{12}$ (each occurrence) independently represent hydrogen or an alkyl group having up to 8 carbon atoms.

13. The complex of item 12 wherein $R_7$ represents an isopropyl group; $R_8$, $R_9$, $R_{10}$, and $R_{12}$ represent hydrogen; and $R_{11}$ represents a methyl group.

14. The complex of item 12 or 13 wherein $R_6$ represents a phenyl group.

15. The complex of any of items 1 to 9 wherein each of $R_1$ and $R_2$ is t-butyl, and each of $R_3$ and $R_4$ is a 2,4,6-trimethylphenyl group.

16. The complex of any of items 1 to 9 wherein each of $R_1$ and $R_2$ is t-butyl, and each of $R_3$ and $R_4$ is a cyclohexyl group.

17. The complex of any of items 1 to 16 wherein the transition metal Mt is selected from Groups 10 to 12 of the Periodic Table of Elements.

18. The complex of item 17 wherein the transition metal Mt is selected from Group 10 of the Periodic Table of Elements.

19. The complex of item 17 wherein the transition metal Mt is nickel or palladium.

20. The complex of item 14 wherein the transition metal Mt is nickel.

21. An olefin polymerization catalyst system comprising the transition metal ligand complex of any of items 1 to 20.

22. The catalyst system of item 21 and further including an activator.

23. The catalyst system of item 22 wherein the activator is tris(pentafluorophenyl)borane.

24. An olefin polymerization catalyst system comprising the transition metal ligand complex of item 20 and a tris(pentafluorophenyl)borane activator.

25. A process for polymerizing at least one monomer comprising contacting said monomer with the catalyst system of any of items 21, 22, or 23.

26. The process of item 25 wherein the monomer comprises ethylene and/or propylene.

27. A process for polymerizing at least one monomer comprising contacting said monomer with the catalyst system of item 24.

28. The process of item 27 wherein the monomer comprises ethylene and/or propylene.

The invention will now be more particularly described with reference to the following non-limiting Examples.

In the Examples, solvents noted as "dry" were dried by passage through columns containing A-2 activated alumina (LaRoche, 8×14 mesh) (ethyl ether and tetrahydrofuran (THF)), or A-2 activated alumina and Q-5 copper reactant (copper oxide on alumina, Engelhard CU-0226S, 14×20 mesh) (toluene, hexanes). See: Pangborn et al. *Organometallics* 1996, 15, 1518-1520. Alternately, they were dried by distillation from sodium benzophenone ketyl (pentane, petroleum ether). NMR solvents were similarly dried over ketyl or $CaH_2$ as appropriate for use with organometallics. Ethylene was obtained from BOC or AGT (4.5 grade, 99.995%) and was used as received. All other chemicals were obtained from commercial sources and used as received. Urea and carbodiimide syntheses utilized the general method of Goodwin after Palomo et al. (see: Goodwin, A. A., "The Synthesis and Characterization of Polycarbodiimides", Ph.D. Thesis, 1996, University of California at Berkeley, and Palomo et al. *Synthesis* 1981, 373-374). $B(C_6F_5)_3$ was obtained from Alfa Aesar Co. and recrystallized from dry pentane.

Solution NMR spectra were obtained using Bruker Avance 400 MHz Ultrashield, Varian Unity Plus 500 MHz, Varian Unity INOVA 300 MHz, or JEOL Delta 400 MHz FT-NMR spectrometers. Cross-polarization (CPMAS) solid-state NMR experiments were carried out using a Chemagnetics CMXII-200 spectrometer with a rotor spinning speed of 3.5 kHz. Correlated rotation and multiple-pulse (CRAMPS) solid-state experiments were performed on a Varian InfinityPlus 500 MHz instrument using a Chemagnetics CRAMPS probe. A REV-8 pulse sequence with a magic angle spinning speed of 2.2 kHz was used. Infrared spectra were obtained on a Mattson Galaxy Series 5000 spectrometer running FIRST software. Stage melting points were determined visually, using grease-sealed capillaries, and are uncorrected. Field Desorption mass spectra were obtained on a VG-ZAB mass spectrometer. Differential Scanning Calorimetry (DSC) data were obtained on a TA Instruments 2920 calorimeter using a scan rate of 10 degrees per minute. Polymer melting points ($T_m$s) reported are taken from the second heat.

EXAMPLE 1

Synthesis of 1,3-di-2,6-diisopropylphenylurea

An oven-dried, 3-necked, 500 mL 24/40 round bottomed flask was charged with 11.6 g (0.0571 mol) 2,6-diisopropylphenyl isocyanate, 290 mL $CHCl_3$, and a large egg-shaped stir bar. The flask was fitted with a vacuum adapter, septum, and an oven-dried addition funnel, which was then charged with 10.1 g (0.0570 mol) 2,6-diisopropylaniline and sealed with a septum. The aniline was added dropwise over a 30 minute period to the stirred isocyanate solution under nitrogen at 0° C. The resultant clear peach solution was allowed to warm to room temperature overnight while stirring. Subsequently, the solution was concentrated to about 80 mL using a rotary evaporator and heated to 70° C., causing formation of a pinkish white solid. This slurry was stirred under nitrogen for 72 hours and was further concentrated. Excess hexanes were added to precipitate a white product, which was collected by filtration and dried under vacuum overnight (19.08 g, 87.9%). $^1H$ NMR ($d_6$-DMSO): δ 7.67 (2H, NH), 7.20 (br tr, 2H) and 7.12 (d, $J_{HH}$=7.32 Hz, 4H) (aryl), 3.29 (br m, 4H, CH), 1.15 (s, 24H, $CH_3$). $^1H$ NMR ($CDCl_3$): δ 7.35 (br tr, $J_{HH}$=6.8 Hz), 7.23 (m), 7.10 (d, $J_{HH}$=8.4 Hz) (aryl, 12H), 6.68 and 5.42 (br s, each 2H, NH), 3.55 and 3.11 (br tr, each 4H, CH), 1.36 (d, $J_{HH}$=7.6 Hz), 1.20 (d, $J_{HH}$=6.0 Hz), 1.16 (br) ($CH_3$, 48 H). $^{13}C\{^1H\}$ NMR ($d_6$-DMSO): δ 155.95 (C=O), 146.64 (aryl ipso), 133.28, 126.83, and 122.73 (aryl), 27.98 ($CH_3$), 23.53 (CH). IR (thin film on NaCl): 3322 (m), 3177 (w), 3067 (w), 2921 (vs), 2934 (sh), 2868 (m), 1678 (s), 1642 (vs), 1589 (w), 1547 (s), 1497 (m), 1466 (m), 1439 (m), 1383 (w), 1362 (w), 1333 (w), 1300 (w), 1260 (w) 1107 (w), 1061 (w), 937 (w), 804 (w), 799 (w), 786 (w), 745 (w), 737 (w), 710 (w) $cm^{-1}$. FD-MS m/z (%): 381.5 ($MH^+$, 100), 762.3 ($M_2H^+$ dimer, 2.5). Exact mass calculated for $C_{25}H_{36}N_2O$: 380.28 (molecular weight 380.56 g/mol). Melting point (DSC): onset (extrapolated) 220° C., max. 222° C.

EXAMPLE 2

Synthesis of 1,3-di-(2,6-diisopropylphenyl)carbodiimide

An oven-dried, 3-necked, 1 L 24/40 round bottomed flask was charged with 300 mL $CH_2Cl_2$, 10.34 g (0.0394 mol) $PPh_3$, and a stirbar. The flask was fitted with a septum, vacuum adapter, and an oven-dried addition funnel, which was charged with 2.02 mL (6.30 g, 0.0394 mol) $Br_2$ diluted with 36 mL $CH_2Cl_2$. The bromine was added dropwise over a 30 minute period to the stirred $PPh_3$ solution under nitrogen at 0° C. The addition funnel was rinsed with an additional 15 mL $CH_2Cl_2$. This rinse was also added to the solution, which became a pale yellow. $Et_3N$ (10.1 mL, 7.98 g, 0.0799 mol) was then added to the solution all at once by a brief removal of the septum on the 3-necked flask. A slight white foam was observed which quickly dissipated. Subsequently, over a 1 hour period, powdered 1,3-di-(2,6-diisopropylphenyl)urea (12.0 g, 0.0315 mol), prepared in accordance with Example 1, was added in solid form to the flask by a similar process. The clear yellow solution turned brown and was stirred overnight at room temperature. Subsequently, 400 mL $CHCl_3$ was added to the flask to precipitate byproducts; however, no precipitates were observed. The solution was extracted with 1×300 mL distilled $H_2O$ to remove triethylammonium bromide, and the organic layer was dried with $Na_2SO_4$, filtered, and depleted of solvent on a rotary evaporator to give a brown crust. Minimal $CHCl_3$ (50 mL) was added to dissolve this material, followed by addition of 600 mL pentane to precipitate $Ph_3P=O$. A milky white suspension containing some brown oil was formed and was filtered after stirring for 1 hour. Removal of pentane from the filtrate gave a yellow oil which slowly solidified to white needles. This material was slurried in 300 mL pentane, and acetone was slowly added (total about 75 mL) until all material had dissolved. Cooling to −15° C. produced 16.93 g of white needles that were identified as $Ph_3P=O$ and removed by decantation. The supernatant (containing the carbodiimide) was depleted of volatiles, and solids were extracted with about 500 mL of petroleum ether. During this procedure, $Ph_3P=O$ continued to precipitate as a sticky solid on the walls of the glassware. A large amount of insolubles from this extraction (2.96 g) were identified as $Ph_3P=O$ and residual urea. The filtrate was further concentrated to about 50 mL and cooled in a −20° C. freezer for 3 h to encourage precipitation of additional $Ph_3P=O$. Filtration of this cold solution, followed by removal of the filtrate volatiles under high vacuum, gave a yellow liquid of crude carbodiimide which slowly solidified (7.32 g, 64%). The product was distilled using a Kugelrohr apparatus at 120-130° C./0.08 mm Hg to give a pale yellow liquid (6.50 g, 56.9%). A very small amount of co-distilling $Ph_3P=O$ remained in the product. $^1H$ NMR ($CDCl_3$): δ 7.11 (br s, aryl, 3 H), 3.47 (septet, $J_{HH}$=6.8 Hz, CH 4H), 1.26 (d, $J_{HH}$=6.8 Hz, $CH_3$, 24H). $^{13}C\{^1H\}$ NMR ($CDCl_3$): δ 142.73 (aryl-o), 133.16 (aryl ipso), 124.84 (aryl-p), 123.22 (aryl-m), 29.09 (CH), 23.20 ($CH_3$). One resonance, presumably the N=C=N peak expected near 140 ppm, was not observed. IR (thin film on NaCl): 3066 (w), 2961 (s), 2930 (m), 2870 (m), 2168 (vs), 1732 (w), 1586 (m), 1460 (s), 1437 (s), 1383 (w), 1364(w), 1327(m), 1256(m), 1182 (in), 1111 (w), 1099(w), 1061 (w), 1042 (w), 934 (w). 806 (sh), 795 (w), 750 (m), 596 (w) cm$^{-1}$. FD-MS m/z (%): 363.5 (MH$^+$, 100). Exact mass calculated for $C_{25}H_{34}N_2$: 362.27 (molecular weight 362.55 g/mol). Melting point (DSC): onset (extrapolated) 46° C., max. 51° C.

EXAMPLE 3

Synthesis of lithium di-(t-butyl)phosphide

In the drybox, di-(t-butyl) phosphine (50 g of 10 wt % solution in hexanes, 34.2 mmol, Strem Co.) was added to a 250 mL Schlenk flask containing a stir bar and 100 mL degassed pentane (dried over molecular sieves). n-Butyl-lithium (14.55 g of 1.6 M solution in hexanes, d=0.680 g/mL, 34.2 mmol) was added while stirring. The flask was sealed with a ground glass stopper and a rubber pipet bulb was placed over the open Schlenk stopcock outlet (to avoid pressure buildup against the stopper). The solution was stirred overnight at room temperature, after which formation of a white precipitate was observed. The precipitate was collected by filtration in the drybox and dried in vacuo to give a pale lemon yellow material (4.371 g, 84%, molecular weight 152.14 g/mol). $^1H$ NMR ($d_8$-THF): δ 1.28 (d of d, $J_{PH}$=10.0 and 1.0 Hz). $^{13}C\{^1H\}$ NMR ($d_8$-THF): δ 37.18 (d, $J_{PC}$=12.8 Hz, $CMe_3$), 31.64 (d, $J_{PC}$=29.3 Hz, $CMe_3$). $^{31}P\{^1H\}$ NMR ($d_8$-THF, vs. 85% aq. $H_3PO_4$): δ 45.51 (s).

EXAMPLE 4

Synthesis of {Li[N,N'-di-(2,6-diisopropylphenyl)-di-(t-butyl)phosphinamidinate]}.$Et_2O$ (Ia)

In the drybox, lithium di-(t-butyl) phosphide (1.018 g, 6.69 mmol), prepared in accordance with Example 3, was dissolved in about 30 mL dry ethyl ether in a round bottomed flask. In a separate 100 mL round bottomed flask, 1,3-di-(2,6-diisopropylphenyl)carbodiimide (2.426 g, 6.69 mmol), prepared in accordance with Example 2 and degassed under high vacuum, was dissolved in about 40 mL dry ethyl ether. An addition funnel was fitted to this flask and charged with the solution of lithium di-(t-butyl) phosphide. This solution was then added dropwise over a one hour period to the carbodiimide solution, resulting in a color change to orange. The solution was allowed to stir for 72 hours after which it was concentrated. Dry hexanes (about 300 mL) were added to the solution, but precipitation of the ligand was not observed. Volatiles were removed to give an orange oily solid which was recrystallized from dry petroleum ether at −40° C. (orange wedges, 1.45 g, 37%, molecular weight of unsolvated species 514.70; molecular weight of solvated species 588.82 g/mol). The $^{13}C\{^1H\}$ and $^{13}C\{^1H, ^{31}P\}$ DEPT-135 spectra of the material were complex due to suspected additional, non-decoupled P—H interactions. $^1H$ NMR ($d_8$-THF): δ 6.96 (v br, 4 H) and 6.75 (v br, 2 H) (aryl), 3.59 (br m, 4 H, CH), 3.41 (q of d, $J_{HH}$=7.0 Hz, $J_{PH}$=0.5 Hz, 4 H, ether $CH_2$), 1.38 (d, $J_{HH}$=10.5 Hz, 24 H, isopropyl $CH_3$), 1.19 (br d, $J_{PH}$=6.0 Hz, 18 H, t-butyl $CH_3$), 1.13 (t of d, $J_{HH}$=7.0 Hz, $J_{PH}$=0.5 Hz, 6 H, ether $CH_3$). $^{13}C\{^1H\}$ NMR ($d_8$-THF, 25° C., assigned by DEPT-135): δ 154.00 (v br s, wk), 141.05 (br s), 123.23 (br s), 120.80 (br s) (aryl and/or NCN, one resonance not observed), 66.21 (tr, $J_{unk}$=15.9 Hz, ether $CH_2$), 34.14 (d, $J_{CP}$=27.2 Hz, t-butyl C), 32.06 (complex tr, app $J_{CP}$=14.9 Hz, t-butyl $CMe_3$ and isopropyl CH), 28.62 (br s, isopropyl $CH_3$), 15.61 (complex d, $J_{unk}$=27.6 Hz, ether $CH_3$). $^{13}C\{^1H\}$ NMR ($d_8$-THF, −10° C.): δ 157.39 (NCN), 154.41, 140.24, 121.15, 116.45 (aryl), remainder of peaks similar to 25° C. spectrum. $^{13}C\{^1H, ^{31}P\}$ DEPT-135 ($d_8$-THF): consistent with $^{13}C$ assignments; due to non-decoupled interactions, the central peak of the triplet at 32.06 has decreased, and singlet at 28.62 now appears as a sidebanded doublet, $J_{unk}$=26.5 Hz. $^{31}P\{^1H\}$ NMR ($d_8$-THF, vs. 85% aq. $H_3PO_4$): δ 38.92 (s).

EXAMPLE 5

Synthesis of

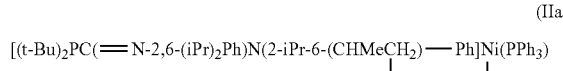

(IIa)

In the drybox, a 50 mL Schlenk flask was charged with 477 mg (0.810 mmol) {Li[N,N'-di-(2,6-diisopropylphenyl)-di-(t-butyl)phosphinamidinate]}.Et$_2$O (Ia), prepared in accordance with Example 4. THF (20 mL) was added to give a yellow solution, followed by a stir bar. (PPh$_3$)$_2$NiPhBr (607 mg, 0.819 mmol; prepared from (PPh$_3$)$_4$N$_1$ and C$_6$H$_5$Br in accordance with Hidai et al. *J. Organomet. Chem.* 1971, 30, 279-282) was added to the ligand solution as a powder, giving a red solution. The flask was sealed and the red solution was stirred for 2 hours at room temperature, after which solvent was removed in vacuo to give a dark brown, taffy-like solid. This material was extracted with 1:1 pentane:toluene (40 mL) overnight. Light orange insolubles (97 mg) were separated by filtration, and volatiles were removed from the dark yellow filtrate to give a dark, filmy solid. Extraction of this material with 40 mL pentane gave the bulk portion of the impure product as bright yellow insolubles (289 g). A smaller but purer fraction of the product was isolated from this pentane filtrate by removal of pentane and subsequent extraction with a smaller volume (10 mL) to give about 0.50 mg (7%) of pure IIa as pentane insolubles, hereinafter referred to as material IIa-1. An attempted recrystallization of the other 289 mg portion of impure material from a mixture of pentane and toluene at −40° C. was unsuccessful, as partial decomposition to unidentified green and black species was observed. The material recovered from this attempt was extracted with 130 mL pentane, filtered to remove insolubles, stripped of solvent under vacuum, and slurried again in about 15 mL pentane. A second crop of pentane-insoluble, bright yellow material was collected (132 mg, 20%), hereinafter referred to as material IIa-2. The spectroscopic properties of IIa-1 and IIa-2 were consistent with the cyclized, N,P-bound structure indicated. $^1$H NMR (CD$_2$Cl$_2$, RT, 500 MHz): δ 7.81 (tr of d, $J_{HH}$=9.0 and 1.5 Hz, 6H, PPh$_3$), 7.44-7.37 (m, 9H, PPh$_3$), 6.84 and 6.72 (each d, $J_{HH}$=7.5 Hz, combined 2H, N-aryl meta), 6.59 and 6.51 (each tr, $J_{HH}$=7.5 Hz, combined 2H, N-arylpara), 6.34 and 6.27 (each d, $J_{HH}$=7.5 Hz, combined 2H, N-aryl meta, 3.40 (sept, $J_{HH}$=6.8 Hz, 1H, isopropyl C HMe$_2$), 3.25 (br sept, $J_{HH}$=3.8 Hz, 1H, CH(Me)CH$_2$—), 2.93 and 2.63 (each sept, $J_{HH}$=6.5 Hz, combined 2H, isopropyl CHMe$_2$), 1.59 (d, $J_{HP}$=13.0 Hz, 9H, CMe$_3$), 1.33 (d, $J_{HH}$=7.0 Hz, 3H, CH(Me)CH$_2$—), 1.22 (d, $J_{HP}$=13.0 Hz, 9H, CMe$_3$), 1.04 (d, $J_{HH}$=6.5 Hz, 6H, isopropyl CHMe$_2$), 1.00, 0.88, 0.78, and 0.66 (each d, $J_{HH}$=6.5 Hz, combined 12H, CHMe$_2$) 0.31 (tr of d, $J_{HH/HP}$=10.5 and 3.3 Hz, 1H, one CH(Me)CH$_2$—). The remaining CH(Me)CH$_2$— resonance was unobserved; however, the C$_6$D$_6$ $^1$H NMR spectrum of the material exhibited two broad triplets at 0.85 ($J_{HH/HP}$=7.0 Hz) and 0.28 ($J_{HH/HP}$=9.3 Hz), each 1H, instead of the resonance at 0.31. $^{13}$C{$^1$H} NMR (CD$_2$Cl$_2$, 25° C., 125 MHz, assigned by DEPT-135/DEPT-90): δ 144.68, 144.58, 140.72, 140.48, 137.95, 137.90 (N-aryl ortho and ipso), 135.02 (d of d, $J_{CP}$=42.1 and 3.6 Hz, PPh$_3$ ipso), 134.53 (d, $J_{CP}$=10.8 Hz), 130.23 (d, $J_{CP}$=2.1 Hz), and 128.40 (d, $J_{CP}$=9.6 Hz) (o, m, p-PPh$_3$), 121.24, 121.00, 120.22, 119.92 (2 C), 119.73 (N-aryl meta and para), 42.17 (d of d, $J_{CP}$=51.5 and 24.4 Hz, CH(Me)CH$_2$—), 34.42 (d, $J_{CP}$=3.8 Hz, CH(Me)CH$_2$—), 33.96 (s) and 33.80 (d, $J_{CP}$=4.8 Hz) (CMe$_3$), 30.77 and 30.22 (each d, $J_{CP}$=6.1 Hz, CMe$_3$), 29.95, 28.87, 27.95 (isopropyl CHMe$_2$), 27.36, 26.64, 24.31, and 21.01 (isopropyl CHMe2) 20.87 (d, $J_{CP}$=6.3 Hz, CH(Me)CH$_2$—), 20.75 and 20.48 (isopropyl CHMe$_2$) (N—C(P)=N not observed). $^{31}$P{$^1$H} NMR (CD$_2$Cl$_2$, 25° C., 202 MHz): δ 45.25 and 43.39 (each d, $J_{PP}$=14.7 Hz, 1P). IR (KBr pellet): 3055 (w), 2947 (s), 2922 (m), 2868 (m), 1591 (w), 1541 (vs, $\upsilon_{C=N}$), 1479 (w), 1435 (m), 1379 (w), 1364 (w), 1323 (w), 1289 (w), 1260 (sh), 1236 (sh), 1182 (w), 1134 (w), 1111 (sh), 1094 (m), 1044 (sh), 1028 (w), 999 (w), 839 (w), 812 (w), 795 (w), 746 (m), 696 (s) cm$^{-1}$ (literature $\upsilon_{C=N}$ for [Ph$_2$PC(N-p-tolyl)(N-p-tolyl)]Mt (PPh$_3$)$_2$: Mt=Rh, 1552 cm$^{-1}$; Mt=Ir, 1562 cm$^{-1}$; Thewissen et al. *J. Organomet. Chem.* 1980, 192, 101-113). FD-MS m/z (%): 826.5 (M+, 100). Exact mass calculated for C$_{51}$H$_{66}$N$_2$PNi: 826.40 (molecular weight 827.73 g/mol). Melting point (stage): 187° C. (dec).

EXAMPLE 6

Synthesis of 1,3-di-(2,4,6-trimethylphenyl)urea 2,4,6-Trimethylphenyl isocyanate (Lancaster Co., 20.5 g, 0.127 mol) and 2,4,6-trimethylaniline (17.2 g, 0.127 mol) were reacted in a procedure analogous to that described in Example 1, giving a brown solution. A thick, white flaky precipitate was observed to form about 2 hours after aniline addition. This material was collected by filtration, rinsed with hexanes, and dried in vacuo (crop 1). The CHCl$_3$ reaction filtrate (also containing rinse hexanes) was set aside and was observed to produce additional white precipitate overnight. It was concentrated somewhat using a rotary evaporator and insolubles were similarly collected by filtration, rinsed with hexanes until a pinkish impurity was removed, and dried (crop 2). Three additional crops of material were collected in this fashion. Crop 3 was collected by removal of volatiles from the filtrate of crop 2, crushing the resultant solid, slurrying it in hexanes overnight, and collecting insolubles by filtration and rinsing them with hexanes. Crop 4 was collected by removal of volatiles from the filtrate of crop 3, slurrying with petroleum ether, and collecting insolubles by filtration and rinsing them with petroleum ether. Crop 5 was collected identically by treatment of the filtrate from Crop 4, using smaller slurry and rinse volumes of petroleum ether. The weights of crops 1 to 5 were 11.1 g, 8.32 g, 5.96 g, 2.30 g, and 4.19 g, respectively (total 31.9 g, 84.6%). $^1$H NMR (solid state CRAMPS, 500 MHz): δ 7.5 (br, aryl), 6.1 and 5.1 (NH), 1.4, 0.9 (sh), and 0.5 (sh) (overlapping, CH$_3$). $^{13}$C{$^1$H} NMR (solid state CPMAS, 50 MHz): δ 157.9 and 154.9 (br, C=0, 1 C), 135.0, 129.6, 128.7, and 127.6 (aryl, 12 C), 22.8, 20.0, 19.4, and 17.9 (CH$_3$, 6 C). IR (KBr pellet): 3286 (vs), 3003 (w), 2972 (m), 2918 (s), 2855 (w), 1640 (vs), 1609 (s), 1553 (vs), 1485 (m), 1470 (sh), 1446 (sh), 1377 (w), 1308 (w), 1285 (w), 1252 (sh), 1223 (s), 1065 (w), 1032 (w), 1013 (w), 882 (w), 849 (m), 760 (w), 748 (w), 721 (sh), 696 (m), 580 (w) cm$^{-1}$. FD-MS m/z (%): 296.7 (MH+, 100). Exact mass calculated for C$_{19}$H$_{24}$N$_2$O: 296.19. Melting point (DSC): onset (extrapolated) 236° C., max. 240° C.

EXAMPLE 7

Synthesis of 1,3-di-(2,4,6-trimethylphenyl)carbodiimide 1,3-Di-(2,4,6-trimethylphenyl)urea (12.0 g, 0.0405 mol, prepared in accordance with Example 6), PPh$_3$ (13.27 g, 0.0506 mol), Br$_2$ (2.07 mL, 6.47 g, 0.0506 mol, diluted for addition with 40 mL CH$_2$Cl$_2$), and Et$_3$N (14.10 mL, 10.24 g, 0.1012 mol) were reacted in a procedure analogous to that described in Example 2, using 400 mL of CH$_2$Cl$_2$ solvent in a 3-necked, 500 mL 24/40 round bottomed flask. The urea did not dissolve in the CH$_2$Cl$_2$ even when the reaction mixture was heated to 42° C. overnight with stirring. The reaction mixture was transferred to a 1 L flask, 500 mL CHCl$_3$ was added, and the CH$_2$Cl$_2$ was removed by distillation at atmospheric pressure. The urea did not dissolve in the CHCl$_3$ even when heated to 60-65° C. The flask was cooled to room temperature, sealed with a septum, and allowed to stir for a period of 10 days, after which no noticeable changes were observed. The mixture was filtered to remove the large quantity of insolubles (presumed to be recovered urea), and the filtrate was extracted with 1×300 mL distilled water, dried over Na$_2$SO$_4$, and depleted of volatiles on a rotary evaporator giving a yellow oil. This oil was extracted with 200 mL petroleum ether, causing precipitation of beige Ph$_3$P═O. Following filtration, the petroleum ether solution was concentrated to about 50 mL, cooled to −20° C. to facilitate precipitation of additional Ph$_3$P═O, and re-filtered. Removal of volatiles from the filtrate gave the crude carbodiimide as a light yellow oil which slowly solidified (6.77 g, 60%). Following Kugelrohr distillation at 120-140° C./0.08 mm Hg, the distilled carbodiimide (6.469 g, 58%) was obtained as a white solid, with a significant aryl-P impurity (CDCl$_3$ $^1$H NMR δ 7.31 ppm (br m); $^{13}$C{$^1$H} NMR δ 137.50 (d, J$_{CP}$=10.6 Hz), 134.03 (d, J$_{CP}$=19.13 Hz), 132.35 (minor, app t, J$_{CP}$~14.4 Hz), 128.99 (s), 128.78 (d, J$_{CP}$=6.9 Hz)). Recrystallization of the distilled material from minimal petroleum ether at −20° C. (filtering the mother liquor through a Nylon filter prior to cooling) gave chunky colorless crystals (3.823 g, 34%) still containing this impurity. The crystals and residual material from the mother liquor (obtained by removal of volatiles) were eluted in 1.5-2 g batches on silica with 5% v/v toluene in hexanes, using a Cyclograph apparatus (silica disc, thickness 1 cm; spin rate 334 rpm, pump flow rate 2.98 at 0-15 mL/min) to give the pure carbodiimide (R$_f$ of carbodiimide~0.55, R$_f$ of impurity ~0.40) (3.051 g, 27%). $^1$H NMR (CDCl$_3$): δ 6.82 (s, 4 H, aryl), 2.33 (s, 12 H, o-Me), 2.24 (s, 6 H, p-Me). $^{13}$C{$^1$H} NMR (CDCl$_3$, assigned by DEPT-135): δ 134.13 and 133.54 (aryl-p and ipso), 132.68 (aryl-o), 129.63 (N═C═N), 129.12 (aryl-m), 21.00 (p-Me), 19.11 (o-Me). IR (thin film on NaCl): 3003 (sh), 2972 (m), 2945 (m), 2918 (m), 2855 (m), 2280 (sh), 2174 (vs), 2064 (sh), 1584 (w), 1476 (s), 1445 (sh), 1377 (w), 1281 (w), 1208 (s), 1146 (m), 1032 (w), 957 (w), 936 (w), 853 (m), 727 (m), 604 (m), 538 (m) cm$^{-1}$. FD-MS m/z (%): 279.3 (MH$^+$, 100). Exact mass calculated for C$_{19}$H$_{22}$N$_2$: 278.18 (molecular weight 279.39 g/mol). Melting point (DSC): onset (extrapolated) 41° C., max. 45° C.

EXAMPLE 8

Synthesis of {Li[N,N'-di-(2,4,6-trimethylphenyl)-di-(t-butyl)phosphinamidinate]} (Ib)

Lithium di-(t-butyl) phosphide (1.12 g, 7.36 mmol, prepared in accordance with Example 3) and 1,3-di-(2,4,6-trimethylphenyl)carbodiimide (2.062 g, 7.41 mmol, prepared in accordance with Example 7 and degassed under high vacuum) were reacted in a total of 70 mL dry ethyl ether in a procedure analogous to that described in Example 4. After a 72 hour period, the resultant solution was pale yellow. Solvent was removed to give a yellow crust, which was slurried in dry petroleum ether overnight, initially giving a lemon yellow, taffy-like solid which became more tractable after pulverization with a spatula and overnight stirring. This material (2.1 g) was isolated by filtration; spectral analysis indicated the presence of a significant phosphorus-containing impurity (30 mol % of total by $^{31}$P{$^1$H} NMR, δ 45.77 (s) in d$_8$-THF vs. 85% aq. H$_3$PO$_4$) and unreacted carbodiimide (11 mol % of total by $^1$H NMR). The P-containing species was initially believed to be unreacted (t-Bu)$_2$PLi based on $^1$H and $^{31}$P{$^1$H} NMR; however, $^{13}$C {$^1$H} NMR showed the absence of the phosphide. Attempted recrystallization of the crude product from hexanes gave an oil, which was isolated by removal of the top hexanes layer and subsequent trituration with petroleum ether for 72 hours giving a white solid (0.42 g, theo. yield 3.19 g, molecular weight of unsolvated species 430.54 g/mol), which was not improved in purity from the initial trituration and showed other unassigned $^1$H, $^{31}$P, and $^{13}$C impurity resonances. Major resonances assigned to product: $^1$H NMR (d$_8$-THF): δ 6.15 (br, appx. 4 H, aryl), 1.99 (br, appx. 18 H, o-Me and p-Me), 1.45 (br, appx. 18 H, t-Bu). $^{13}$C{$^1$H} NMR (d$_8$-THF, −10° C.): δ 130.3-127.5 (br, aryl, not all aryl or NCN observed/assigned), 32.86 (br s, t-butyl C), 31.31 (br s, CMe$_3$), 21.42 (br s, p-Me), 20.63 (s, o-Me). $^{31}$P{$^1$H} NMR (d$_8$-THF, vs. 85% aq. H$_3$PO$_4$): δ 53.76 (s).

EXAMPLE 9

Synthesis of {Li[N,N'-dicyclohexyl-di-(t-butyl) phosphinamidinate]} (Ic)

Lithium di-(t-butyl) phosphide (1.11 g, 7.30 mmol, prepared in accordance with Example 3) and 1,3-dicyclohexylcarbodiimide (1.50 g, 7.27 mmol, degassed under high vacuum overnight) were reacted in a total of 70 mL dry ethyl ether in a procedure analogous to that described in Example 4. Immediate precipitation of a white product was observed. The reaction mixture was stirred for 2.5 days at room temperature, and the white insoluble product was collected by filtration and washed with dry diethyl ether (2.3 g, 88%). This material was ground to a powder in the drybox using a mortar and pestle, slurried in 50 mL dry diethyl ether for several hours to remove impurities, collected by filtration, and dried in vacuo (1.95 g, 74%, molecular weight of unsolvated species 358.47 g/mol). $^1$H NMR (d$_8$-THF): δ 3.47 and 3.29 (each br tr, 1 H, cyclohexyl CHN), 3.37 (q, J$_{HH}$=7.0 Hz, minor, residual ether CH$_2$), 1.88 (d, J$_{HH}$=11.5 Hz, 2H) and 1.76 (d, J$_{HH}$=11.5 Hz, 2H), 1.72, 1.67, 1.64, 1.61, 1.58, 1.55, and 1.53 (each br s, total 6 H) (cyclohexyl CH$_2$), 1.25 (d, J$_{PH}$=11.0, 18 H, CMe$_3$), 1.38-1.06 (br m, 8 H, cyclohexyl CH$_2$+residual ether CH$_3$), 0.89 (q, J$_{HH}$=11.5 Hz, 2 H, cyclohexyl CH$_2$). $^{13}$C{$^1$H} NMR (d$_8$-THF, assigned by full DEPT sequence): δ 162.58 (d, J$_{CP}$=43.5 Hz, N—C═N), 57.88 (d, J$_{CP}$=69.0 Hz) and 57.68 (br d, J$_{CP}$=7.5

Hz) (cyclohexyl CHN), 38.28 (d, $J_{CP}$=69.0 Hz, cyclohexyl CH$_2$ α to CHN), 32.32 (d, $J_{CP}$=16.4 Hz, CMe$_3$), 30.90 (d, $J_{CP}$=11.1 Hz, CMe$_3$), 27.75 (s, cyclohexyl CH$_2$ γ to CHN), 26.62 (d, $J_{CP}$=42.5 Hz, cyclohexyl CH$_2$ β to CHN). $^{31}$P{$^1$H} NMR (d$_8$-THF, vs. 85% aq. H$_3$PO$_4$): δ 45.91 (s).

EXAMPLES 10 TO 12

Polymerization of Ethylene at 120 Psig (0.83 MPa) using IIa and B(C$_6$F$_5$)$_3$ Activator The following general procedure was used. Reaction parameters and results are given in Table 1. In the drybox, 7 mg (0.0085 μmol) Ia (batch IIa-1 or IIa-2 as noted), prepared in accordance with Example 5, was dissolved in approximately ½ of the noted total dry solvent volume in a glass vial. In a separate vial, the noted amount of B(C$_6$F$_5$)$_3$ (21.7 mg, 41.7 μmol, 5 eq., or 43.5 mg, 83.7 mmol, 10 eq.) was dissolved in the remaining dry solvent, and this solution was charged into an air-tight syringe. A 70 mL glass Fischer-Porter vessel was charged with the Ia solution and a stirbar and was sealed with a head apparatus featuring a pressure gauge, septum syringe port, and vent valve. The sealed pressure bottle apparatus was removed from the glove box, heated to the noted temperature (if not room temperature) in an oil bath, attached to an ethylene manifold, and pressurized to 120 psig (0.83 MPa) ethylene. The bottle was vented to ambient pressure and the pressurization/venting procedure repeated twice to ensure flushout of residual argon from the vessel. The activator solution was then injected into the bottle using the syringe port. The bottle was resealed and pressurized to a constant 120 psig (0.83 MPa) ethylene and allowed to stir overnight (about 16 hours) at the noted temperature. Subsequently, the bottle was vented to ambient pressure, and the polymerization was quenched with a small amount (1-5 mL) of methanol injected through the syringe port. The bottle was opened, its contents were added to an excess of clean methanol, and the precipitated polymer was collected by filtration, rinsed with additional methanol, and dried in a vacuum oven at 60° C. overnight. IR of polyethylene obtained in Example 10 (KBr pellet): 2934 (vs), 2911 (vs), 2851 (s), 1464 (m), 1377 (w), 721 (m) cm$^{-1}$. IR of polyethylene obtained in Example 11 (KBr pellet): 2920 (vs), 2851 (s), 1472 (m), 1377 (w), 1262 (w), 1094 (w), 1024 (w), 802 (w), 723 (m) cm$^{-1}$. IR of polyethylene obtained in Example 12 (KBr pellet): 2913 (vs), 2849 (s), 1467 (s), 1377 (w), 1306 (w), 1242 (m), 1155 (w), 986 (w), 719 (m) cm$^{-1}$. The polymer samples were insoluble for Gel Permeation Chromatography (GPC) analysis in 1,2,4-trichlorobenzene at 135° C.

EXAMPLE C1

(Control) Polymerization of Ethylene at 120 Psig (0.83 MPa) in the Absence of IIa The process of Examples 10 to 12 was repeated, but with material IIa being omitted. Instead of performing three ethylene pressurization/vent cycles prior to injection of B(C$_6$F$_5$)$_3$ solution, the pressure vessel was pressurized once to 120 psig (0.83 MPa) ethylene, held at this pressure for 1 minute, vented, and then repressurized following B(C$_6$F$_5$)$_3$ injection. No polyethylene was obtained. Results are shown in Table 1.

EXAMPLE 13

Polymerization of Ethylene at 600 Psig (4.14 MPa) using IIa and B(C$_6$F$_5$)$_3$ Activator In the drybox, an oven-dried 300 mL glass Parr reactor liner was charged with 18 mg (0.0217 mmol) material IIa-2 and 25 mL dry pentane. Separately, 55.7 mg (0.109 mmol, 5 eq.) B(C$_6$F$_5$)$_3$ was dissolved in 5 mL dry pentane in a glass vial, and this solution was charged into an air-tight syringe. The glass liner was fitted into a 300 mL Hasteloy C Parr reactor equipped with a mechanical stirrer and syringe port, and the reactor was assembled and sealed, removed from the drybox, and attached to an ethylene manifold. After purging gas connections and initiating mechanical stirring, the reactor was pressurized to 600 psig (4.14 MPa) ethylene pressure for 2 minutes and vented to ambient pressure. The activator was quickly injected using the syringe port, and the reactor was again pressurized to a constant 600 psig (4.14 MPa) ethylene pressure and allowed to stir overnight (about 16 hours) at room temperature. Subsequently, the reactor was vented to ambient pressure, and the polymerization was quenched with a small amount (1-5 mL) of methanol injected through the syringe port. The reactor was opened, its contents were added to an excess of clean methanol, and the precipitated polymer was collected by filtration, rinsed with additional methanol, and dried in a vacuum oven at 60° C. overnight. Results are shown in Table 1.

TABLE 1

| Ex. No.[a] | Catalyst batch | μmol cat. (conc.) | Solvent | Activator | psig C$_2$H$_4$ | T (° C.)[b] | Yield PE (g) | T$_m$ (° C.) (ΔH$_f$ (J/g))[c] |
|---|---|---|---|---|---|---|---|---|
| 10 | IIa-1 | 8.5 (1.7 mM) | 5 mL toluene | 5 eq. B(C$_6$F$_5$)$_3$ | 120 | RT | 0.018 | 115.7 (br) 120.3 |
| 11 | IIa-1 | 8.5 (2.1 mM) | 4 mL pentane | 5 eq. B(C$_6$F$_5$)$_3$ | 120 | RT | 0.080 | 121.3 (135.7) |
| 12 | IIa-2 | 8.5 (1.7 mM) | 5 mL pentane | 10 eq. B(C$_6$F$_5$)$_3$ | 120 | 50 | 0.020 | 113.7 (br) 107.4 |
| C1 | — | — | 4 mL pentane | 5 eq. B(C$_6$F$_5$)$_3$[d] | 120 | RT | — | — |
| 13 | IIa-2 | 21.7 (0.7 mM) | 30 mL pentane | 5 eq. B(C$_6$F$_5$)$_3$ | 600 | RT | 0.040 | 126.9 (154.7) |

120 psig = 0.83 MPa; 600 psig = 4.14 MPa.
Br = broad transition.
[a]Run duration = overnight (about 16 hours).
[b]RT = Room temperature (no thermostatting).
[c]DSC, 2$^{nd}$ heat.
[d]Same molar amount as used in Examples 10-12.

The invention claimed is:

1. A transition metal ligand complex having the following formula:

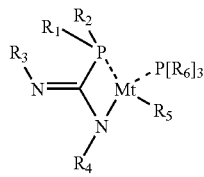

wherein $R_1$ and $R_2$ (each occurrence) independently represent an aryl, alkyl, or cycloalkyl group having up to 20 carbon atoms; $R_3$ and $R_4$ (each occurrence) independently represent an aryl, alkyl, or cycloalkyl group having up to 20 carbon atoms; $R_5$ represents an aryl, alkyl, or cycloalkyl group having up to 20 carbon atoms, provided that $R_4$ and $R_5$ may be joined to form a cyclic structure; $R_6$ represents an alkyl or aryl group having up to 20 carbon atoms; and Mt represents a transition metal selected from the group consisting of Groups 7, 8, 9, 10, 11, and 12 of the Periodic Table of the Elements.

2. The complex of claim 1 wherein one or each of $R_1$ and $R_2$ represents a t-butyl group.

3. The complex of claim 1 wherein one or each of $R_3$ and $R_4$ represents an aryl group.

4. The complex of claim 3 wherein one or each of $R_3$ and $R_4$ represents an aryl group bearing an alkyl substituent having up to 8 carbons at one or both of the ortho (2,6-) positions to the respective aryl-N bond.

5. The complex of claim 4 and bearing said alkyl substituents at both of the ortho (2,6-) positions to the respective aryl-N bond.

6. The complex of claim 5 wherein each alkyl substituent is independently selected from methyl and isopropyl.

7. The complex of claim 5 wherein each alkyl substituent is isopropyl.

8. The complex of claim 1 wherein $R_5$ represents a phenyl group.

9. The complex of claim 1 wherein $R_6$ represents a phenyl group.

10. The complex of claim 1 wherein $R_4$ and $R_5$ are joined to form a cyclic structure.

11. The complex of claim 10 wherein $R_4$ represents an aryl group bearing an alkyl substituent having up to 8 carbons at one or both of the ortho (2,6-) positions to the aryl-N bond, and $R_4$ and $R_5$ are joined such that the complex has the following formula:

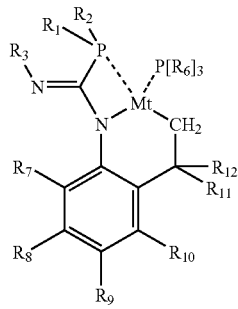

wherein $R_1$ and $R_2$ (each occurrence) independently represent an aryl, alkyl, or cycloalkyl group having up to 20 carbon atoms; $R_3$ represent an aryl, alkyl, or cycloalkyl group having up to 20 carbon atoms; $R_6$ represents an alkyl or aryl group having up to 20 carbon atoms; Mt represents a transition metal selected from the group consisting of Groups 7, 8, 9, 10, 11, and 12 of the Periodic Table of the Elements; and $R_7$, $R_8$, $R_9$, $R_{10}$, $R_1$, and $R_{12}$ independently represent hydrogen or an alkyl group having up to 8 carbon atoms.

12. The complex of claim 11 wherein $R_7$ represents an isopropyl group; $R_8$, $R_9$, $R_{10}$, and $R_{12}$ represent hydrogen; and $R_{11}$ represents a methyl group.

13. The complex of claim 12 wherein $R_6$ represents a phenyl group.

14. The complex of claim 1 wherein each of $R_1$ and $R_2$ is t-butyl, and each of $R_3$ and $R_4$ is a 2,4,6-trimethylphenyl group.

15. The complex of claim 1 wherein each of $R_1$ and $R_2$ is t-butyl, and each of $R_3$ and $R_4$ is a cyclohexyl group.

16. The complex of claim 1 wherein the transition metal Mt is selected from Groups 10 to 12 of the Periodic Table of Elements.

17. The complex of claim 1 wherein the transition metal Mt is selected from Group 10 of the Periodic Table of Elements.

18. The complex of claim 1 wherein the transition metal Mt is nickel or palladium.

19. The complex of claim 13 wherein the transition metal Mt is nickel.

* * * * *

UNITED STATES PATENT AND TRADEMARK OFFICE
CERTIFICATE OF CORRECTION

PATENT NO. : 7,351,845 B2 Page 1 of 1
APPLICATION NO. : 11/333639
DATED : April 1, 2008
INVENTOR(S) : Lisa S. Baugh et al.

It is certified that error appears in the above-identified patent and that said Letters Patent is hereby corrected as shown below:

Please delete "Ia" at column 23, line 14 and add -- IIa --.

Please delete "Ia" at column 23, line 21 and add -- IIa --.

Signed and Sealed this

Eleventh Day of August, 2009

David J. Kappos
*Director of the United States Patent and Trademark Office*